United States Patent
Yotsutsuji (10) Patent No.: US 11,446,442 B2
(45) Date of Patent: Sep. 20, 2022

(54) GASKET AND SYRINGE HAVING THE SAME

(71) Applicant: Coki Engineering Inc., Osaka (JP)

(72) Inventor: Akira Yotsutsuji, Osaka (JP)

(73) Assignee: COKI ENGINEERING INC., Osaka (JP)

( * ) Notice: Subject to any disclaimer, the term of this patent is extended or adjusted under 35 U.S.C. 154(b) by 299 days.

(21) Appl. No.: 16/637,793

(22) PCT Filed: Aug. 29, 2017

(86) PCT No.: PCT/JP2017/030922
§ 371 (c)(1),
(2) Date: Feb. 10, 2020

(87) PCT Pub. No.: WO2019/043784
PCT Pub. Date: Mar. 7, 2019

(65) Prior Publication Data
US 2020/0215269 A1    Jul. 9, 2020

(51) Int. Cl.
*A61M 5/315* (2006.01)
*A61M 5/31* (2006.01)

(52) U.S. Cl.
CPC ...... *A61M 5/31515* (2013.01); *A61M 5/3129* (2013.01); *A61M 5/31513* (2013.01);
(Continued)

(58) Field of Classification Search
CPC ............ A61M 5/31515; A61M 5/3129; A61M 2005/3131; A61M 2205/0222; A61M 2205/0216; A61M 5/31513
See application file for complete search history.

(56) References Cited

U.S. PATENT DOCUMENTS

| 3,581,956 A | 6/1971 | Reid |
| 10,058,658 B1 * | 8/2018 | Voytilla ............ A61M 5/31515 |

(Continued)

FOREIGN PATENT DOCUMENTS

| CN | 201586295 U | 9/1999 |
| GB | 2494683 A | 3/2013 |

(Continued)

OTHER PUBLICATIONS

CNIPA, Office Action for corresponding Chinese Patent Application No. 201780094153.9, dated May 28, 2021, with English translation.
(Continued)

*Primary Examiner* — Bradley J Osinski
(74) *Attorney, Agent, or Firm* — Lucas & Mercanti, LLP (57) ABSTRACT

A gasket suitable for a syringe stopping with vacuum is provided. The gasket is compatible with sliding property within the sleeve and water-tightness of the syringe barrel after exiting the sleeve. The gasket includes a gasket body made of a liquid-resistant hard plastic having a tip surface contacting medicinal solution and a concave groove formed on a side surface facing an inner peripheral surface of a syringe barrel and formed continuously to the tip surface contacting medicinal solution; and a sliding contact ring made of an elastic material fitted in the concave groove. Then, an outer diameter D1 of a peripheral end of a tip portion including the tip surface contacting medicinal solution of the gasket body is set to be larger than the outer diameter D4 of the sliding contact ring.

4 Claims, 9 Drawing Sheets

(52) U.S. Cl.
CPC . *A61M 5/31511* (2013.01); *A61M 2005/3104* (2013.01); *A61M 2005/3131* (2013.01); *A61M 2205/0222* (2013.01); *A61M 2205/0238* (2013.01)

(56) References Cited

U.S. PATENT DOCUMENTS

| | | | |
|---|---|---|---|
| 2007/0060896 A1 | 3/2007 | Miller et al. | |
| 2010/0204658 A1* | 8/2010 | Imai | A61M 5/31513 604/222 |
| 2015/0148751 A1* | 5/2015 | Yotsutsuji | A61M 5/31513 604/218 |

FOREIGN PATENT DOCUMENTS

| | | |
|---|---|---|
| JP | H11-47275 A | 2/1999 |
| JP | 2009505794 A | 2/2009 |
| JP | 5406416 B1 | 2/2014 |
| WO | 1999/044659 A1 | 9/1999 |
| WO | 2007027585 A2 | 3/2007 |
| WO | 2009001600 A1 | 12/2008 |
| WO | 2016/113409 A1 | 7/2016 |

OTHER PUBLICATIONS

International Search Report dated Oct. 17, 2017 for Application No. PCT/JP2017/030922 and English translation.
KIPO, Office Action for corresponding Korean Patent Application No. 10-2020-7004979, dated Dec. 6, 2021, with English translation.
EPO, Extended European Search Report for corresponding European Patent Application No. 17922951.3, dated May 18, 2020.
First Examination Report of corresponding Indian Patent Application No. 202027008993 dated Mar. 7, 2022, with English translation.
CNIPA, Office Action for corresponding Chinese Patent Application No. 201780094153.9, dated Dec. 10, 2021, with English translation.

* cited by examiner

GASKET AND SYRINGE HAVING THE SAME

CROSS REFERENCE TO RELATED APPLICATION

This Application is a 371 of PCT/JP2017/030922 filed on Aug. 29, 2017, which is incorporated herein by reference.

TECHNICAL FIELD

The present invention relates to a gasket suitable for a "syringe vacuum plugging method using a sleeve" and to a syringe having the same.

BACKGROUND OF THE INVENTION

For example, the Patent Document 1, Japanese Patent Application Laid-Open Publication No. 2009-505794, shows a gasket having high safety and sealing property over a long period of time in a state where medicinal solution is injected. And the gasket has low sliding resistance against to a syringe barrel.

The gasket (i.e. plunger tip) for the syringe disclosed in the Patent Document 1 has a gasket body (i.e. core) in which a concave groove is formed on a side peripheral surface facing an inner peripheral surface of the syringe barrel, and a sliding contact ring (i.e. raised portion) fitted in the concave groove.

In addition, by using material hardly affecting quality of the medicinal solution for the gasket body that comes into direct contact with the medicinal solution, and by selectively using material having high slide ability with respect to the syringe barrel for the sliding ring, it is possible to obtain slide ability capable of pushing the gasket with light force while minimizing the influence on the quality of the medicinal solution.

CITATIONS LIST

Patent Document 1: JP 2009-505794T
Patent Document 2: JP H11-47275A

SUMMARY OF THE INVENTION

However, the conventional gasket described above also has other problems. That is, the gasket may not be suitable for the syringe vacuum plugging method using a sleeve. The syringe vacuum plugging method using a sleeve is described in, for example, Patent Document 2: Japanese Patent Application Laid-Open No. H11-47275.

The "syringe vacuum plugging method using a sleeve" will be briefly described. The syringe vacuum plugging method using a sleeve is conducted by inserting a gasket into a metal cylindrical sleeve in advance, and inserting one end of the sleeve from above into a syringe barrel into which medicinal solution has been injected in advance in a vacuum state of a predetermined degree. The sleeve is then raised relative to the syringe barrel and the gasket so that the gasket exiting the sleeve remains within the syringe barrel. At this time, by the elasticity of the gasket itself, the side surface of the gasket body and the sliding contact ring constituting the gasket are in close contact with an inner peripheral surface of the syringe barrel, thereby sealing the medicinal solution. The manufacture of the syringe has been completed.

In relation to the "syringe vacuum plugging method using a sleeve" conducted by such a flow, at least an outer diameter of one end portion of the sleeve needs to be formed smaller than the inner diameter of the open end portion of the syringe barrel. Therefore, the gasket is radially compressed in the one end portion of the sleeve having the smallest diameter until it comes out of the one end portion of the sleeve. And the gasket comes into close contact with the inner peripheral surface of the syringe barrel. Then the gasket slides in the sleeve under a predetermined pressing force even under this compression. After the gasket comes out of the sleeve, the gasket is required to expand by its own elasticity and seal (water-tight) the inside of the syringe barrel.

As described above, the gasket disclosed in Patent Document 1 keeps water-tightness by contacting the sliding contact ring of the gasket to the inner peripheral surface of the syringe barrel. Furthermore, the outer diameter of the sliding contact ring in a natural state is formed to be larger than the outer diameter of the gasket body mainly for the purpose of ensuring the slide ability and water-tightness of the gasket in the syringe barrel. The natural state means a state in which the gasket is not fitted in the sleeve or the syringe barrel.

In general, the thickness of the sliding contact ring is smaller than the thickness of the gasket body. The thickness of the sliding contact ring means the distance between the outer end and the opposing inner end in the radial direction of the sliding contact ring. And the thickness of the gasket body means the distance from the center to the outer end in the radial direction of the gasket body. Therefore, the restoring property of the sliding contact ring is smaller than the restoring property of the gasket body. The restoring property means the degree of returning to the dimension before compression when it is expanded again by its own elasticity after being compressed to a predetermined dimension.

Therefore, when a conventional gasket is applied to the "syringe vacuum plugging method using a sleeve", if the outer diameter of the sliding contact ring in the natural state is set so that the gasket slides within the sleeve with a predetermined pressing force, there is a possibility that a problem that the water-tightness of the syringe barrel after the gasket is pulled out of the sleeve arises. And conversely, if the outer diameter of the sliding contact ring is set large to such an extent that no water-tightness problem of the syringe arises, there is a possibility that a problem that the gasket does not slide easily within the sleeve arises.

The present invention has been developed in view of the problems of the prior art. It is therefore a principal object of the present invention to provide a gasket suitable for the "syringe vacuum plugging method using a sleeve" which is compatible with sliding within the sleeve and with the water-tightness of the syringe barrel after the gasket has been pulled out from the sleeve.

According to an aspect of the present invention,

A gasket comprises:

a gasket body made of a medicinal solution-resistant hard plastic and having a tip surface contacting medicinal solution and a concave groove formed on a side surface facing an inner peripheral surface of a syringe barrel and formed continuously to the tip surface contacting medicinal solution; and a sliding contact ring made of an elastic material fitted in the concave groove, wherein an outer diameter of a peripheral end of a leading portion of the gasket body including the tip contact liquid surface is larger than an outer diameter of the sliding contact ring.

Preferably, when the gasket is fitted in the syringe barrel, a peripheral edge portion of the tip surface contacting medicinal solution of the gasket body contacts against an inner peripheral surface of the syringe barrel.

Preferably, the peripheral edge portion of the tip surface contacting medicinal solution contacts the inner peripheral surface of the syringe barrel on a surface elongated by being bent the peripheral edge portion in a state that the gasket body is fitted in the syringe barrel.

Preferably, the gasket body is formed by the Cold forming.

Preferably, the material of the gasket body is PTFE, and the material of the sliding contact ring is silicone rubber to which sliding property is added.

Preferably, the gasket is used for a syringe vacuum plugging method using a sleeve.

According to another aspect of the present invention,

A syringe includes a gasket as described above is provided.

According to the gasket of the present invention, the outer diameter of the peripheral end at the tip portion including the tip surface contacting medicinal solution of the gasket body is set to be larger than the outer diameter of the sliding contact ring. Therefore, when the gasket is fitted in the sleeve, the sliding contact ring is compressed in the radial direction, and the peripheral end portion of the tip portion of the gasket body is compressed in the radial direction so as to bend toward the rear end surface side of the gasket body and slightly cover a tip portion side of the sliding contact ring. Then, when the gasket is fitted into the syringe barrel, the outer peripheral surface of the sliding contact ring and the peripheral edge portion of the tip surface contacting medicinal solution of the gasket body comes into contact the inner peripheral surface of the syringe barrel.

As described above, regarding the gasket of the present invention, the water-tightness of the syringe barrel is ensured by the peripheral edge portion of the tip surface contacting medicinal solution of the gasket body contacting on the inner peripheral surface of the syringe barrel. The restoring property of the gasket body is greater than the restoring property of the sliding contact ring. After the diameter of the gasket body and the sliding contact ring is greatly reduced in the radial direction as the gasket passes through the sleeve, the gasket body attempts to restore to a greater degree than the sliding ring. Therefore, the water-tightness in the syringe barrel is easily ensured when the gasket is fitted into the syringe barrel having an inner diameter slightly larger than the outer diameter of the sleeve. The present invention provides a gasket suitable for the "syringe vacuum plugging method using a sleeve" which was compatible with both sliding property within the sleeve and water tightness of the syringe barrel by the gasket after exiting the sleeve.

DETAILED DESCRIPTION OF THE INVENTION (Structure of a Gasket 10 and a Syringe 100)

A gasket 10 in accordance with an embodiment of the present invention and a syringe 100 including the gasket 10 will be described in accordance with the illustrated embodiment.

Figure 1:
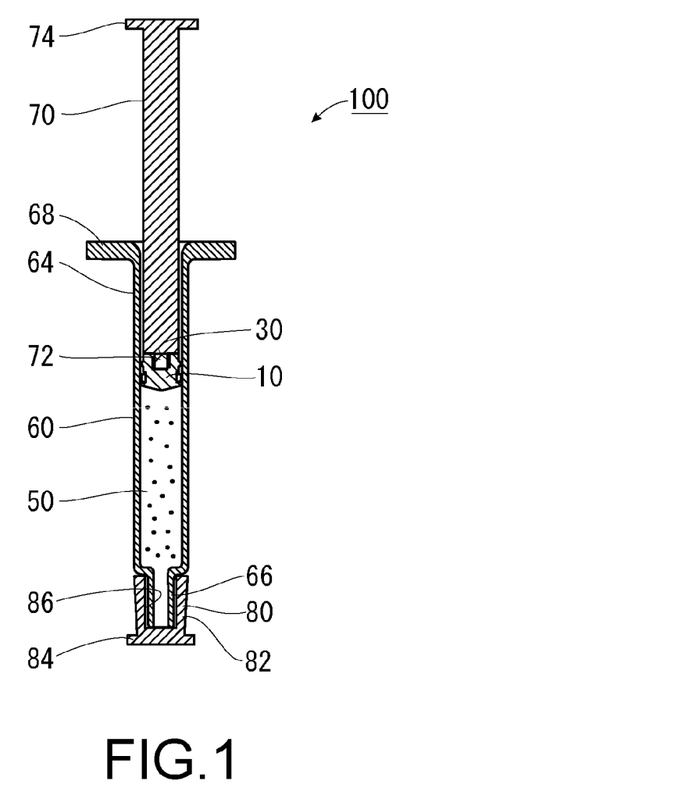
FIG. 1 is a cross-sectional view showing the syringe 100 in accordance with an embodiment of the present invention.

As shown in FIG. 1, the syringe 100 includes a gasket 10, medicinal solution 50, a syringe barrel 60, a piston rod 70, and a top cap 80.

Figure 2:
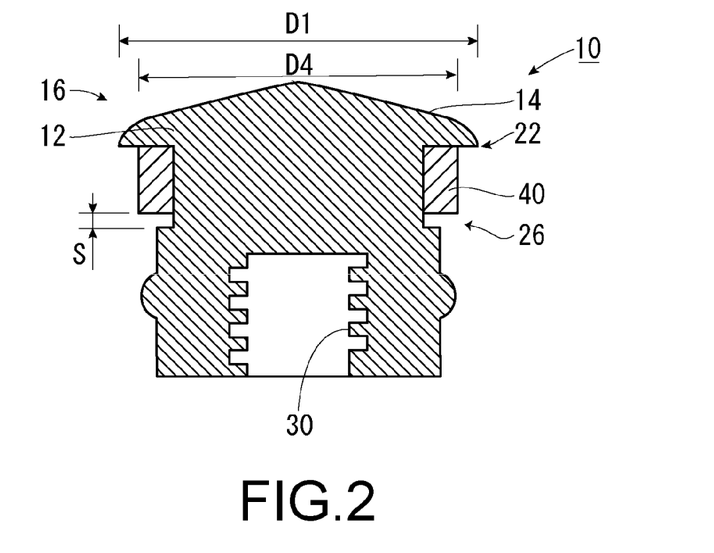
FIG. 2 is a cross-sectional view showing the gasket 10 in accordance with an embodiment of the present invention.

As shown in FIG. 2, the gasket 10 includes a gasket body 12 and a sliding contact ring 40.

Figure 3:
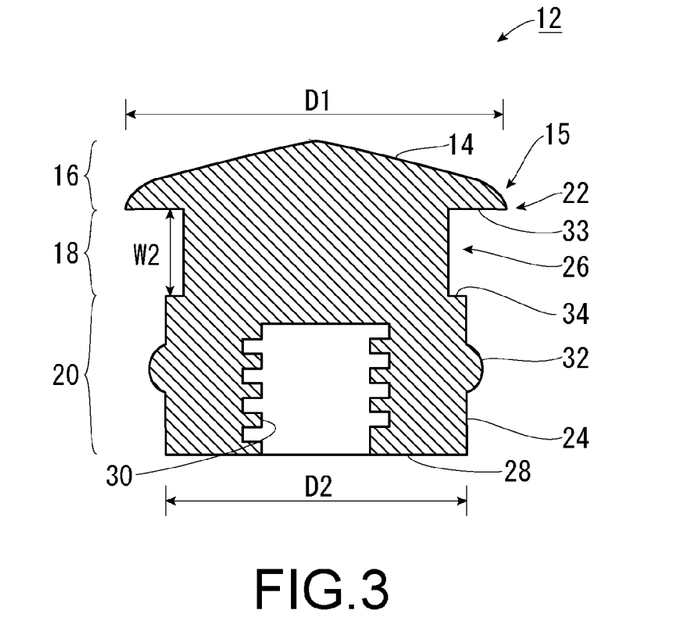
FIG. 3 is a cross-sectional view showing the gasket body 12 in accordance with an embodiment of the present invention.

As shown in FIG. 3, the gasket body 12 includes a tip end surface (referred to herein as "a tip surface contacting medicinal solution 14") that comes into contact with the medicinal solution 50 when the gasket 10 is fitted into the syringe barrel 60. The gasket body 12 also includes a tip portion 16 that is formed in an umbrella shape and has an outer diameter that increases as it approaches the rear end side, a small diameter portion 18 that is rapidly reduced in diameter in a step shape continuing the tip portion 16, and an enlarged diameter portion 20 that is increased in diameter in a step shape continuing the small diameter portion 18.

As described above, since the step is formed between the tip portion 16 and the small diameter portion 18, a trailing end side of the tip portion 16 has the largest outer diameter and has an angular shape. In this specification, the trailing end side of the tip portion 16 having the largest outer diameter is referred to as a peripheral end 22.

Further, since steps are formed between the tip portion 16 and the small diameter portion 18 and between the small diameter portion 18 and the enlarged diameter portion 20, a part corresponding to the small diameter portion 18 becomes a concave groove 26 formed over the entire circumference of the side surface 24 of the gasket body 12. The step between the tip portion 16 and the small diameter portion 18 is referred to as a leading side step 33, and the step between the small diameter portion 18 and the enlarged diameter portion 20 is referred to as a trailing end side step 34.

Further, the outer diameter D1 of the peripheral end 22 of the tip portion 16 is formed to be larger than the outer diameter D2 of the enlarged diameter portion 20. That is, in the gasket body 12, the outer diameter D1 of the peripheral end 22 is formed to be the largest.

A screw hole 30 for mounting the piston rod 70 is formed in the rear end face 28 of the gasket body 12. Further, a ridge portion 32 protruding toward a side direction of the gasket body 12 is formed on the surface of the enlarged diameter portion 20 over the entire circumference of the side surface 24 of the enlarged diameter portion 20. The ridge portion 32 has an outer diameter substantially equal to or slightly smaller than the inner diameter of the syringe barrel 60. As a result, the ridge portion 32 serves as a guide for preventing a central axis of the gasket 10 from being largely displaced from a central axis of the syringe barrel 60 when the gasket 10 slides within the syringe barrel 60. The ridge portions 32 may be provided at least three places on the side surface 24 of the enlarged diameter portion 20, instead of the entire circumference of the side surface 24 of the enlarged diameter portion 20. The three ridges 32 are preferably disposed at equal angles to each other on a plane perpendicular to the central axis of the gasket body 12. The central axis of the gasket body 12 means that the central axis along the direction of travel through the syringe barrel 60.

The method of molding the gasket body 12 is not particularly limited, and may be, for example, cutting using a lathe or the like, or injection molding. It is preferable to form the gasket body 12 by the "Cold forming" method as described in "Modification 1" which will be described later.

The gasket body 12 is entirely formed of a hard material (a hard plastic having chemical resistance) that does not react with the medicinal solution 50 such as a fluorine resin, PTFE (polytetrafluoroethylene), PFA (tetrafluoroethylene-perfluoroalkylvinylether copolymer), FEP (a copolymer of ethylene tetrafluoride and propylene hexafluoride), PCTFE (polychlorotrifluoroethylene), PVDF (polyvinylidene fluoride), PP (polypropylene), ultra-polymer polyethylene, COP (cycloolefin polymer), or COC (ethylene norbornene copolymer). For example, the gasket body 12 of the present embodiment is formed of PTFE.

The hardness of the hard plastic material is preferably 70 or more in Shore A hardness (or 40 to 100 in Shore D hardness and 40 to 70 in Rockwell M hardness).

The PTFE used in the present embodiment may be pure PTFE. But it is more preferable to use a modified substance in which 1 to 15% by weight of a fluorine resin is mixed. The fluorine resin is, for example, such as a polytetrafluoroethylene-perfluoroalkyl vinyl ether copolymer (abbreviated as PFA) or a tetrafluoroethylene-hexafluoropropylene copolymer, which is a crystallization inhibitor of PTFE. By using the modified substance, the gasket body 12 obtains elasticity.

A pure PTFE or a modified PTFE can be used for this embodiment. Further, a closed-cell block (or round bar) formed by a hot isostatic pressing (HIP) process also be used for this embodiment.

The primary sintered block of the PTFE is obtained by compression-molding pure PTFE powder or modified PTFE powder and sintering the compression-molded powder. In this sintering, the contact portions between the powders are in close contact with each other, but very fine gaps are formed in the non-contact portions. As a whole, the minute fluids are passed through the continuous fine gaps.

When the primary sintered block of this PTFE is pressed by the hot isostatic pressing, the primary sintered block of the PTFE is compressed, and the ultrafine gaps existing between the grains of the PTFE are reliably closed, and closed cells are formed. Further, the hot isostatic pressing under reduced pressure is more effective.

Figure 4:
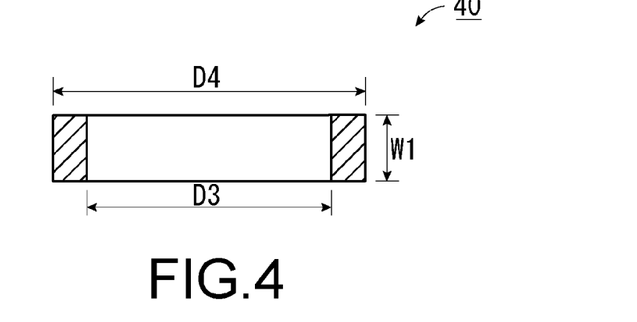
FIG. 4 is a cross-sectional view showing the sliding contact ring 40 in accordance with an embodiment of the present invention.

Next, the sliding contact ring 40 will be described. As shown in FIG. 4, the sliding contact ring 40 is a ring-shaped member having a rectangular cross-sectional shape. And the inner diameter D3 of the sliding contact ring 40 is set to be substantially the same size or slightly smaller than the outer diameter of the small diameter portion 18 of the gasket body 12. The outer diameter D4 of the sliding contact ring 40 is set to be smaller than the outer diameter D1 of the peripheral end 22 of the tip portion 16 of the gasket body 12 and larger than the outer diameter D2 of the enlarged diameter portion 20.

The width W1 of the sliding contact ring 40 is set smaller than the width W2 of the small diameter portion 18 of the gasket body 12. See FIG. 3. In other words, the width W1 of the sliding contact ring 40 is set smaller than the width W2 of the concave groove 26 formed on the gasket body 12. Therefore, when the sliding contact ring 40 is fitted into the concave groove 26, a gap S is formed between the side surface of the sliding contact ring 40 and at least one of the steps of the gasket body 12, as shown in FIG. 2.

Figure 13:
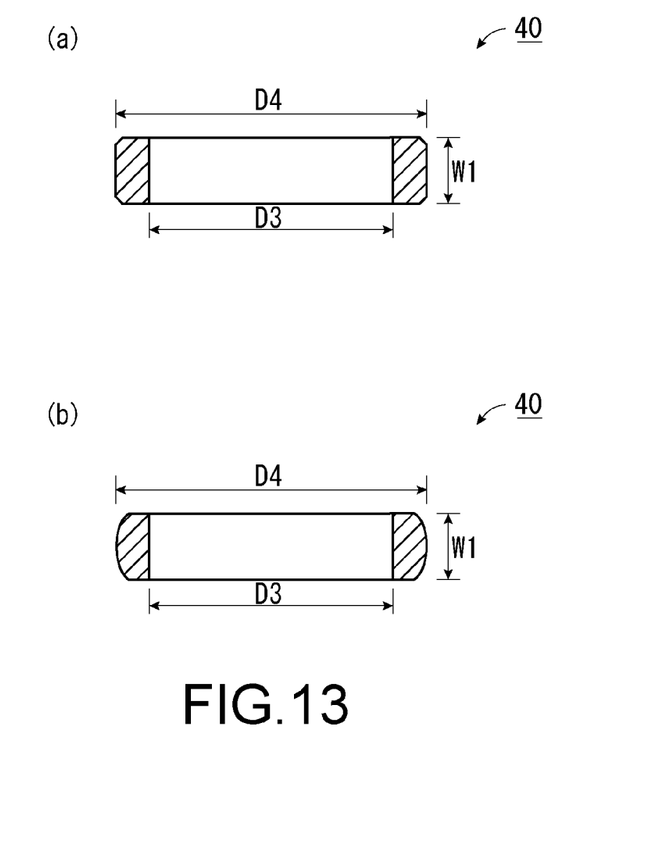
FIG. 13 is a cross-sectional view showing the sliding contact ring 40 in accordance with another embodiment.
Figure 14:
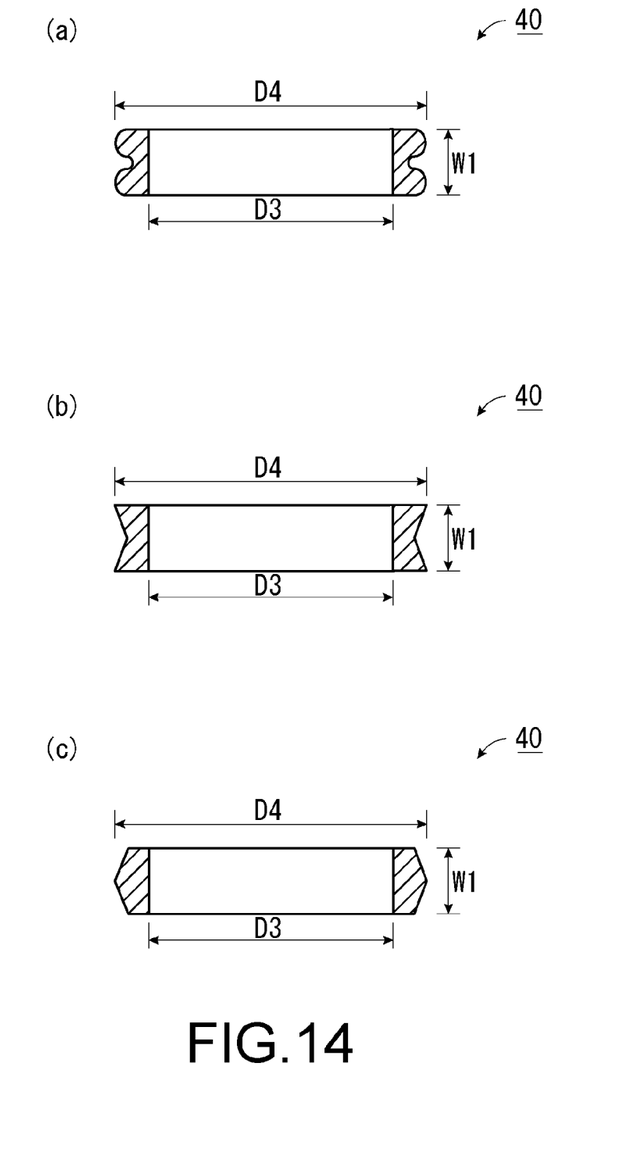
FIG. 14 is a cross-sectional view showing the sliding contact ring 40 in accordance with yet another embodiment.

The shape of the sliding contact ring 40 is not limited to that of the present embodiment. And the shape of the sliding contact ring 40 may be, for example, a shape in which an outer end corner is chamfered as shown in FIG. 13(a), or may be an arc-shaped outer circumferential surface cross-sectional shape in which the central portion in the width direction has the maximum diameter as shown in FIG. 13(b). Further, as shown in FIG. 14(a), the outer peripheral surface of the sliding contact ring 40 may be defined by the cross-sectional shape of the waveform. And the cross-sectional shape of the outer peripheral surface of the sliding contact ring 40 may be tapered such that the central portion in the width direction has the minimum diameter as shown in FIG. 14(b). Further, as shown in FIG. 14(c), the cross-sectional shape of the outer peripheral surface of the sliding contact ring 40 may be tapered such that the central portion in the width direction has the maximum diameter. In either shape, the maximum outer diameter of the sliding contact ring 40 is the outer diameter D4.

The sliding contact ring 40 of the present embodiment is formed of elastic material. Since the gasket 10 of the present embodiment is used for the syringe 100, it is preferable that the elastic material forming the sliding contact ring 40 is already approved as a medical member, and for example, "silicone rubber" to which sliding property is imparted.

The "silicone rubber" is a thermosetting resin. And "organopolysiloxane" in a liquid state, a grease state, or a clay state as a raw material is a material in which a methyl group, a vinyl group, a phenyl group, or a trifluoropropyl group is incorporated in a molecule, and each is used when special characteristics are required. There are several types of "silicone rubber". In the present embodiment, any of them can be used. Here, as an example, a peroxide crosslinked silicone rubber is used. This peroxide crosslinked silicone rubber contains a liquid or grease "organopolysiloxane" containing a vinyl group. By adding a necessary filling and a peroxide curing agent, kneading, and curing to a target molecular weight, the peroxide crosslinked silicone rubber is formed. Another example is an addition reaction type silicone rubber. This addition reaction type silicone rubber is formed by heating and curing two types of clay polysiloxane by a reaction using platinum, rhodium, or an organic compound of tin as a catalyst. One type of polysiloxane contains a vinyl group incorporated in a molecule. The other type of polysiloxane contains a reactive hydrogen incorporated in a molecular terminal.

The silicone rubber having the sliding property is formed, for example, by adding a peroxide (or the curing catalyst and the above two kinds of clay-like polysiloxanes) as a cross-linking agent to a liquid, grease, or clay-like organosiloxane, adding a predetermined amount of silicone oil, and kneading with a kneader. In order to adjust the hardness of the kneaded material, an appropriate amount (for example, 25%) of fine silica powder is added as necessary. If necessary, for example, a predetermined amount of ultra high molecular weight polyethylene fine powder is added.

The polyethylene resin forming the fine particles of the fine powder is an ultra-high polymer. For example, the average molecular weight of such ultra-high polymer is 1 million to 3 million or more and up to 7 million. Such ultra-high molecular weight particles are not permeable to water and do not adhere to most of things. Because of its too high molecular weight, the ultra high molecular weight polyethylene does not melt even at a high temperature. As a result, the ultra high molecular weight polyethylene retains its spherical shape even when molded at a high pressure. The surface of the spherical ultra high molecular weight polyethylene is relatively smooth, but some irregularities are also observed. The range of the particle diameter of the spherical ultra high molecular fine particles contained in the fine powder is 10 to 300 µm. More preferably, the range of the particle diameter is 20 to 50 µm. Depending on a grade, an average particle size of 25 µm, 30 µm or other may be used. In the case where the range of the particle size distribution is wide, the small particle size enters between the large particle size and fills the gap between the large particle size. As a result, the fine filling is realized. Regarding the fine filling, since the fine particles do not have water permeability, even if a silicone rubber base material or silicone oil having water permeability is used, the medical slidable silicone rubber of the present invention as a whole has very low water permeability.

The silica fine powder is a powder made of silica sand as a raw material, and most of the silica powder is made of silicon (SiO2). It is added to the elastic material in order to adjust its hardness.

A molding method of the sliding contact ring 40 will be described. The intended sliding contact ring 40 is formed through the thermal crosslinking after 1 to 10 minutes by heating and pressing a molding material described above filled into a compression mold heated to an appropriate temperature. The molding material means the silicone rubber kneaded by adding silica powder, silicone oil, and ultra high molecular weight PE powder added as necessary. The sliding contact ring 40 is preferably subjected to secondary heat treatment (annealing).

Returning to FIG. 1, the syringe barrel 60 is a cylindrical container. A mounting portion 66 to which an injection needle (not shown) is mounted is protruded from the tip of the barrel body 64. And a flange 68 for finger-hanging is formed at a rear end of the barrel body 64. As a hard resin, for example, cycloolefin resin (COP), polypropylene (PP), ethylene norbornene copolymer (COC), or the like, is used for the material of the syringe barrel 60 in addition to glass. Since the gasket 10 of the present embodiment can structurally maintain a high water-tightness of the syringe barrel 60 as described later, the glass syringe barrel 60 which is inferior in inner diameter dimensional accuracy to the resin can also be used.

The piston rod 70 is a rod-shaped member in which a male thread portion 72 is formed at a tip end portion thereof and a finger-pushing portion 74 is formed at a rear end portion thereof. The male thread portion 72 of the piston rod 70 is formed with a male screw that can be screwed into the screw hole 30 formed in the gasket body 12 of the gasket 10. A resin such as cyclic polyolefin, polycarbonate, polypropylene, or the like can be used for the material of the piston rod 70.

The top cap 80 includes a frusto-conical cap body 82 and a disk-shaped cap flange 84 extending laterally from the top end of the cap body 82. The cap body 82 is formed with a recess 86 into which the mounting portion 66 of the syringe barrel 60 is fitted. The top cap 80 is formed of an elastomer. A film having chemical resistance (PTFE or PFA) is laminated on the inner peripheral surface of the top cap 80. The Elastomer means vulcanized rubber, thermoset elastomers, thermoplastic elastomers, or the like.

(Procedure for Manufacturing of the Syringe 100)

Next, a procedure for manufacturing the syringe 100 by the syringe vacuum plugging method using a sleeve using the gasket 10 of the present embodiment will be explained. The syringe vacuum plugging method using a sleeve has an advantage in that, unlike a vacuum plugging injection conducted in a vacuum container, air bubbles do not easily mix into the medicinal solution 50 at the time of the plugging, because the plugging can be conducted under the low vacuum degree.

Figure 5:
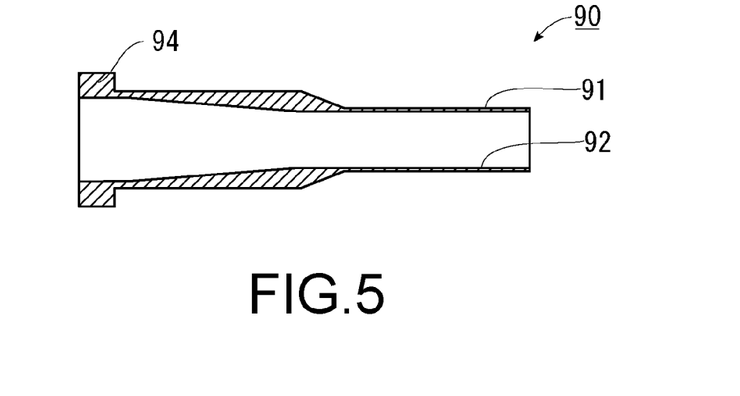
FIG. 5 is a cross-sectional view of an embodiment of a sleeve 90 for use in the "syringe vacuum plugging method using a sleeve".

A sleeve 90 made of metal as shown in FIG. 5 is used for the syringe vacuum plugging method using a sleeve. In the present embodiment, the sleeve 90 is made of stainless steel whose surface and inner surface are mirror-polished. The sleeve 90 includes a pipe-shaped sleeve body 91 and a sleeve flange 94 extending laterally on the inlet end side for which the gasket 10 is inserted into the sleeve body 91. The outer diameter of the sleeve body 91 is formed such that the inlet end side into which the gasket 10 is inserted is thick, and the outlet end side from which the gasket 10 is out is narrower. The outlet end side will be inserted into the syringe barrel 60. A part of the inner surface 92 of the sleeve body 91 is tapered so that the inner diameter of the sleeve body 91 is smaller at the outlet end than at the inlet end.

Figure 6:
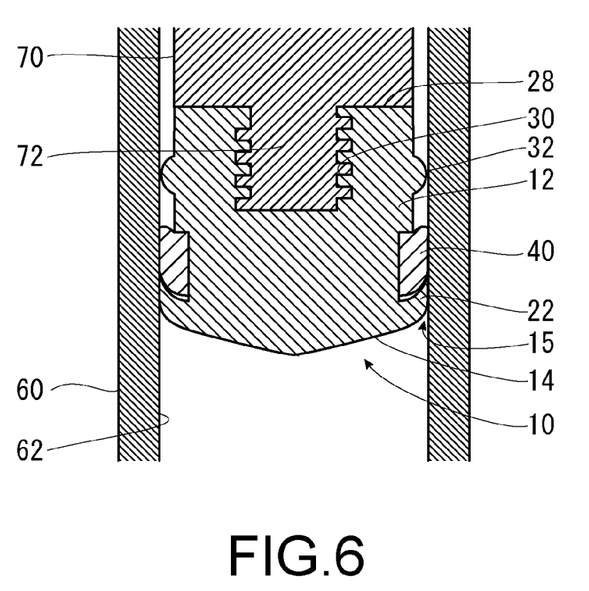
FIG. 6 is a cross-sectional view of an embodiment of the gasket 10 fitted in the syringe barrel 60.

By the syringe vacuum plugging method using a sleeve, the gasket 10 is fitted into the syringe barrel 60, as shown in FIG. 6. FIG. 6 also shows a state in which the male thread portion 72 of the piston rod 70 is screwed into the screw hole 30 of the gasket body 12.

Figure 7:
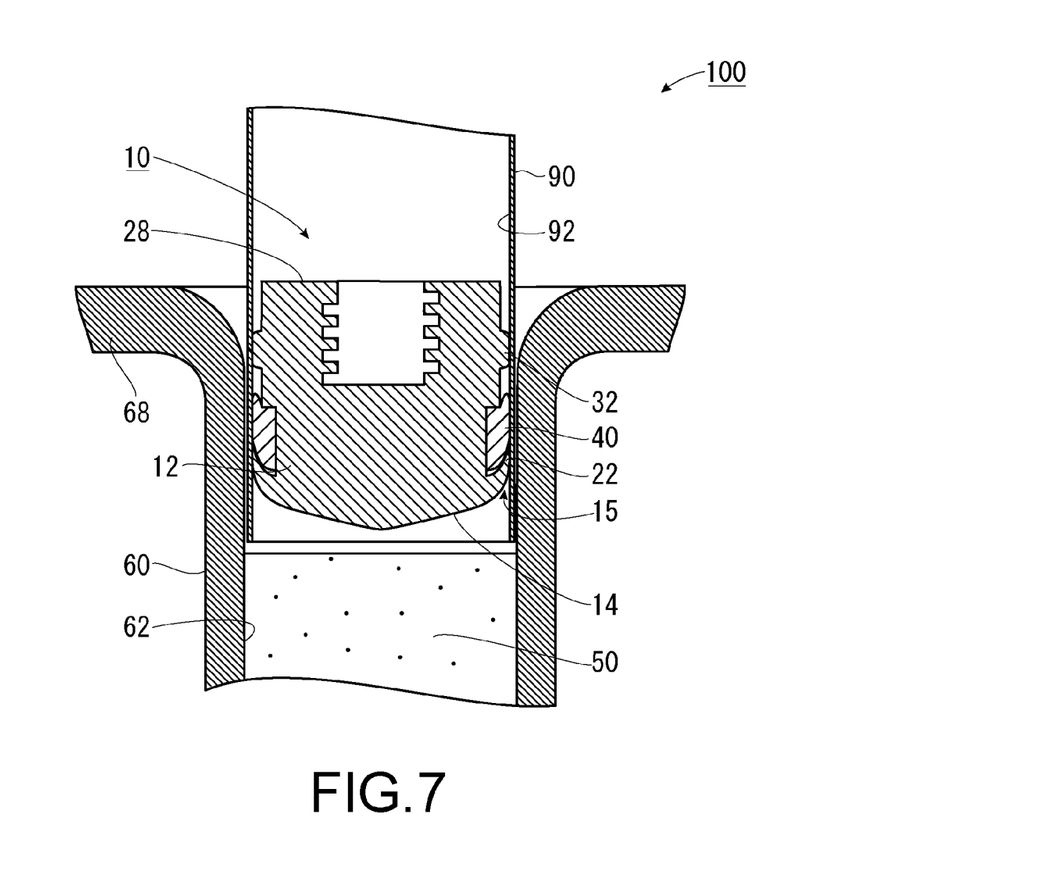
FIG. 7 is a cross-sectional view illustrating the syringe vacuum plugging method using a sleeve using the gasket 10 in accordance with an embodiment of the present invention.

As shown in FIG. 7, the gasket 10 is previously fitted into the sleeve 90 from the inlet end of the sleeve 90 in a state in which the tip surface contacting medicinal solution 14 is directed toward the syringe barrel 60 before the syringe vacuum plugging method using a sleeve. At this time, the gasket body 12 and the sliding contact ring 40 of the gasket 10 are respectively fitted in the sleeve 90 in a radially compressed state. As described above, in the gasket 10 of the present embodiment, the outer diameter D1 of the peripheral end 22 in the tip portion 16 of the gasket body 12 is set to be larger than the outer diameter D4 of the sliding contact ring 40. And the outer diameter D4 of the sliding contact ring 40 is set slightly larger than the inner diameter of the sleeve 90. As a result, when the gasket 10 is fitted into the sleeve 90, the sliding contact ring 40 is compressed in the radial direction, and the peripheral end 22 of the gasket body 12 is compressed in the radial direction so as to being bent toward the rear end face 28. And the peripheral end 22 of the gasket body 12 slightly covers the tip portion 16 side of the sliding contact ring 40. That is, the outer peripheral surface of the sliding contact ring 40 contacts against the inner surface 92 of the sleeve 90, and the peripheral edge portion 15 of the tip surface contacting medicinal solution 14 of the gasket body 12 bends toward the rear end face 28. Thereby the peripheral edge portion 15 contacts against the inner surface 92 of the sleeve 90.

Figure 8:
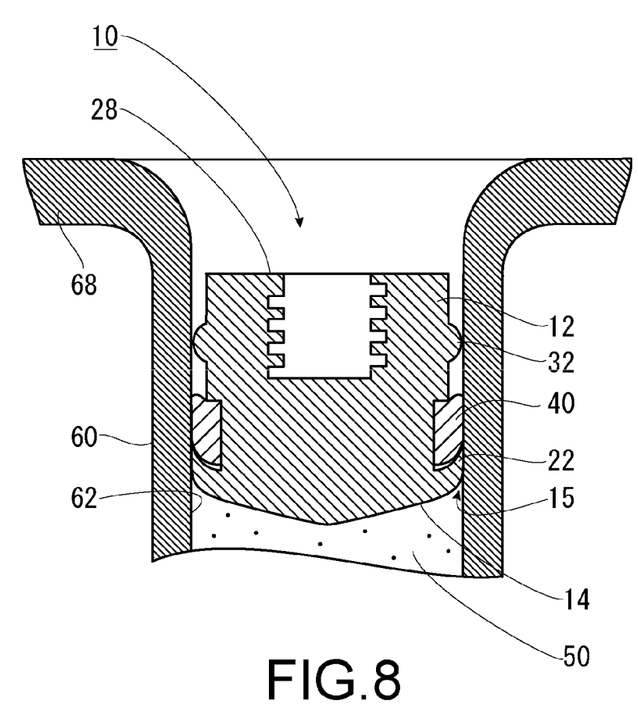
FIG. 8 is a cross-sectional view showing the syringe 100 completed with the syringe vacuum plugging method using a sleeve.

In this state, the top cap 80 is attached to the mounting portion 66 of the syringe barrel 60 in advance. And the tip end portion of the sleeve 90 is inserted into the syringe barrel 60 filled with the medicinal solution 50. Then, the rear end face 28 of the gasket body 12 is pressed by a rod-shaped member such as a piston keeping a positional relationship between the syringe barrel 60 and the gasket body 12 unchanged, and only the sleeve 90 is moved upward (i.e., in a direction away from the syringe barrel 60). As a result, the gasket 10 slides within the sleeve 90 while keeping the positional relationship with the syringe barrel 60. And finally, as shown in FIG. 8, the gasket 10 comes out of the outlet end of the sleeve 90. Then the outer peripheral surface of the sliding contact ring 40 and the peripheral edge portion 15 of the tip surface contacting medicinal solution 14 of the gasket body 12 contact on the inner peripheral surface 62 of the syringe barrel 60.

(Features of Gasket 10)

(1)

According to the gasket 10 of the present embodiment, the outer diameter of the peripheral end 22 of the tip portion 16 of the gasket body 12 is set to be larger than the outer diameter of the sliding contact ring 40. As a result, when the gasket 10 is fitted into the sleeve 90, the sliding contact ring 40 is compressed in the radial direction. And the peripheral end 22 portion of the gasket body 12 is compressed in the radial direction so as to being bent toward the rear end face 28 and cover the corner portion of the sliding contact ring 40 on the tip portion 16 side. When the gasket 10 is finally fitted into the syringe barrel 60, the outer peripheral surface of the sliding contact ring 40 and the peripheral edge portion 15 of the tip surface contacting medicinal solution 14 of the gasket body 12 come into contact with the inner peripheral surface 62 of the syringe barrel 60.

In the case of the gasket 10 of the present embodiment, the water-tightness of the syringe barrel 60 is ensured by the peripheral edge portion 15 of the tip surface contacting medicinal solution 14 of the gasket body 12 that comes into contact with the inner peripheral surface 62 of the syringe barrel 60. As described above, since the thickness of the gasket body 12 is larger than the thickness of the sliding contact ring 40, the restoring property of the gasket body 12 is larger than the restoring property of the sliding contact ring 40. Therefore, even if the diameter of the gasket body 12 and the sliding contact ring 40 is greatly reduced in the radial direction when passing through the sleeve 90, when the gasket body 12 enters the syringe barrel 60 having an inner diameter slightly larger than the outer diameter of the sleeve 90, the gasket body 12 attempts to restore to a larger size than the sliding contact ring 40, so that the water-tightness in the syringe barrel 60 can be easily ensured.

(2)

In addition, when a side surface of a conventional gasket body is brought into contact with the inner peripheral surface 62 of the syringe barrel 60 to ensure the water-tightness as in the conventional gasket, it is necessary to determine the outer diameter of the side surface of the gasket body in considering with the restoring property of the dimension after comes out from the sleeve 90. High accuracy will be required for such a design and molding. This is because, if the outer diameter of the side surface of the gasket body after exiting the sleeve 90 is small relative to the inner diameter of the syringe barrel 60, the water-tightness of the syringe barrel 60 cannot be ensured. Conversely, if the outer diameter of the side surface of the gasket body after exiting the sleeve 90 is made sufficiently large relative to the inner diameter of the syringe barrel 60, the gasket must be pushed by an excessive force when the gasket is inserted through the sleeve 90.

In this regard, in the gasket 10 of the present embodiment, since the outer diameter of the peripheral end 22 of the tip portion 16 of the gasket body 12 is set to be larger than the outer diameter of the sliding contact ring 40, the gasket body 12 contacts the inner surface 92 of the sleeve 90 and the inner peripheral surface 62 of the syringe barrel 60 at the peripheral edge portion 15 of the tip surface contacting medicinal solution 14 by bending the peripheral end 22 of the tip portion 16 toward the rear end face 28 side of the gasket body 12. At this time, since the sliding contact ring 40 is disposed on the rear end face 28 side of the peripheral end 22 of the tip portion 16 and a gap S is formed between the side surface of the sliding contact ring 40 and at least one step (the leading side step 33 or the trailing end side step 34) of the gasket body 12, it is possible to receive the peripheral end 22 of the gasket body 12 bent to the rear end face 28 side by the sliding contact ring 40, and it is possible to prevent the peripheral end 22 from being bent to the rear end face 28 side more than necessary.

As a result, when the gasket 10 is inserted into the sleeve 90, the gasket 10 fits to the inner diameter of the sleeve 90 by the relatively large bending of the peripheral end 22. And when the gasket 10 exits the sleeve 90, and the gasket 10 fits to the inner peripheral surface 62 of the syringe barrel 60, which is larger than the inner diameter of the sleeve 90, by the relatively smaller bending of the peripheral end 22 than when the gasket 10 is inserted into the sleeve 90.

Further, in the gasket 10 of the present embodiment, as described above, the peripheral edge portion 15 of the tip surface contacting medicinal solution 14 of the gasket body 12 contacts on the inner surface 92 of the sleeve 90 and the inner peripheral surface 62 of the syringe barrel 60. A surface of the peripheral edge portion 15 elongated by being bent the peripheral end 22 of the gasket body 12 toward the rear end face 28 in a state in which the gasket 10 is fitted into the syringe barrel 60 contacts on the inner surface 92 of the sleeve 90 and the inner peripheral surface 62 of the syringe barrel 60. Therefore, the surface having a roughness smaller than that of before the gasket body 12 is elongated can contacts the inner surface 92 and the inner peripheral surface 62. As a result, the water-tightness of the syringe barrel 60 can be ensured with higher accuracy as compared with the case where the side surface of the gasket body as in the conventional gasket contacts on the inner peripheral surface 62 of the syringe barrel 60.

(Modification 1)

The above-described gasket body 12 is preferably molded by the "Cold forming" method. The "Cold forming" refers to processing and forming into a desired shape by applying pressure and generated heat to the base material under a temperature at which the base material does not melt. The processing and forming are conducted at a temperature, for example, about 20° C. to 200° C. when the base material is PTFE.

The gasket body 12 formed by the "Cold forming" has a "memory effect (re-memory)". The "memory effect (re-memory)" is a characteristic that the gasket body 12 deformed by an external force returns to the original shape when heat is applied.

As a result, when the syringe 100 that has been plugged with the syringe vacuum plugging method using a sleeve by using the gasket body 12 molded by the "Cold forming" is heated in steam for sterilization or disinfection, the bent peripheral end 22 attempts to return to the original shape. The original shape means a state in which the degree of bending is smaller by the "memory effect (re-memory)". The state in which the degree of bending is smaller means the diameter of the peripheral end 22 is larger. The medicinal solution 50 may be, for example, a "contrast agent". As a result, the peripheral edge portion 15 of the tip surface contacting medicinal solution 14 of the gasket body 12 is pressed more strongly against the inner peripheral surface 62 of the syringe barrel 60. Then the water-tightness of the syringe barrel 60 is further enhanced.

(Modification 2)

Figure 9:
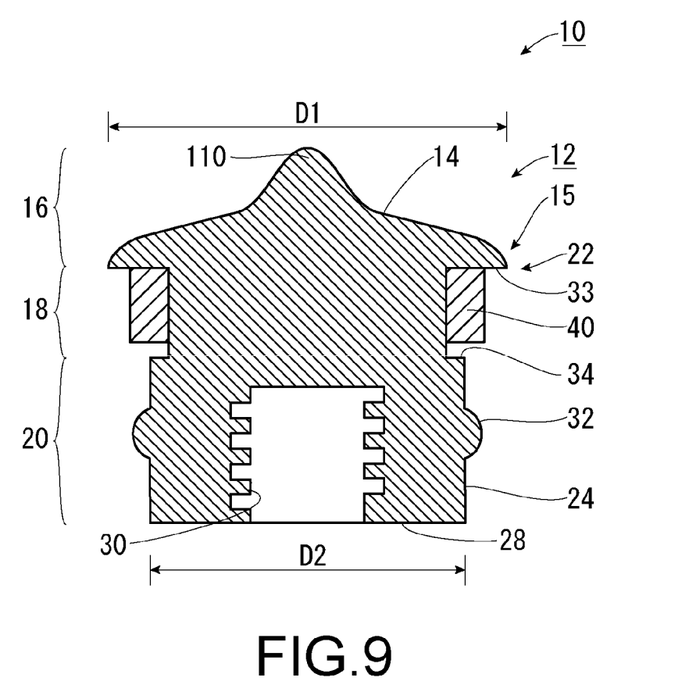
FIG. 9 is a cross-sectional view showing the gasket 10 in accordance with another embodiment.
Figure 10:
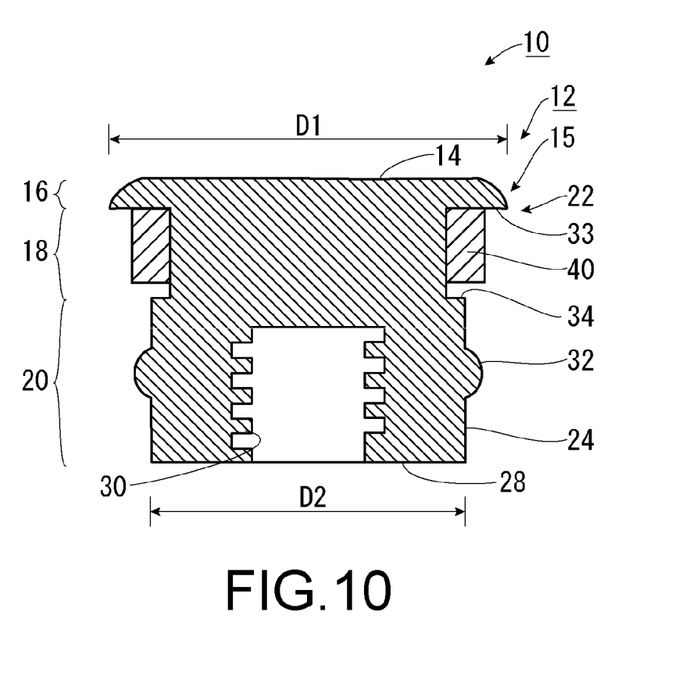
FIG. 10 is a cross-sectional view showing the gasket 10 in accordance with yet another embodiment.

The shape of the gasket body 12 is not limited to the shape of the above-described embodiment, and may be, for example, as shown in FIG. 9, such a shape that the gasket body 12 has a conical protrusion 110 protruding from a substantially central portion of the tip surface contacting medicinal solution 14. By providing the protrusion 110 in this manner, when the medicinal solution 50 is injected into a patient or the like using the syringe 100 in which the medicinal solution 50 is filled in the syringe barrel 60, the protrusion 110 enters the inner space of the mounting portion 66 in the syringe barrel 60. By entering the inner space, it is preferable in that more medicinal solution 50 can be injected. In addition, in the shape of the gasket body 12 as shown in FIG. 10, the tip surface contacting medicinal solution 14 may be formed in a planar shape.

Figure 11:
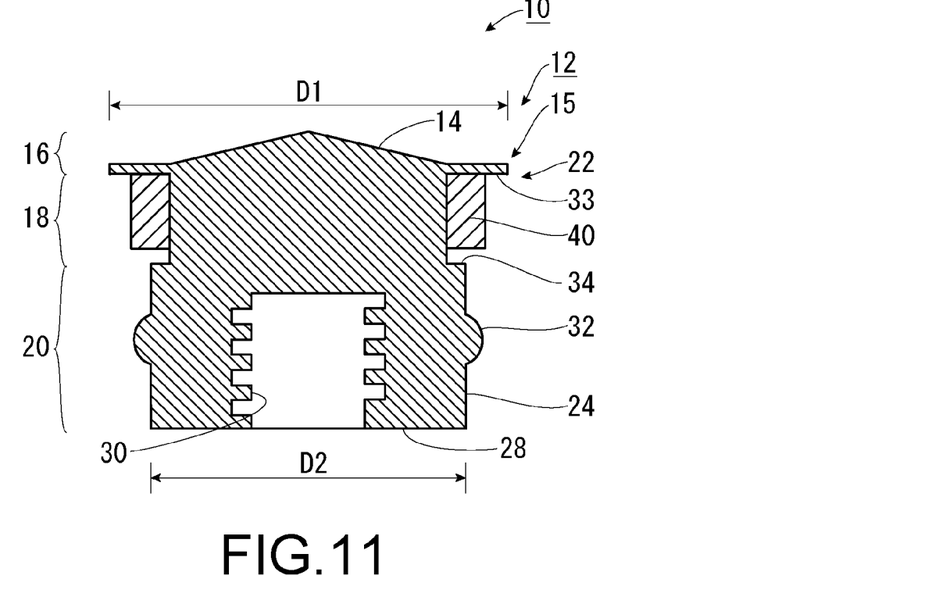
FIG. 11 is a cross-sectional view showing the gasket 10 in accordance with yet another embodiment.
Figure 12:
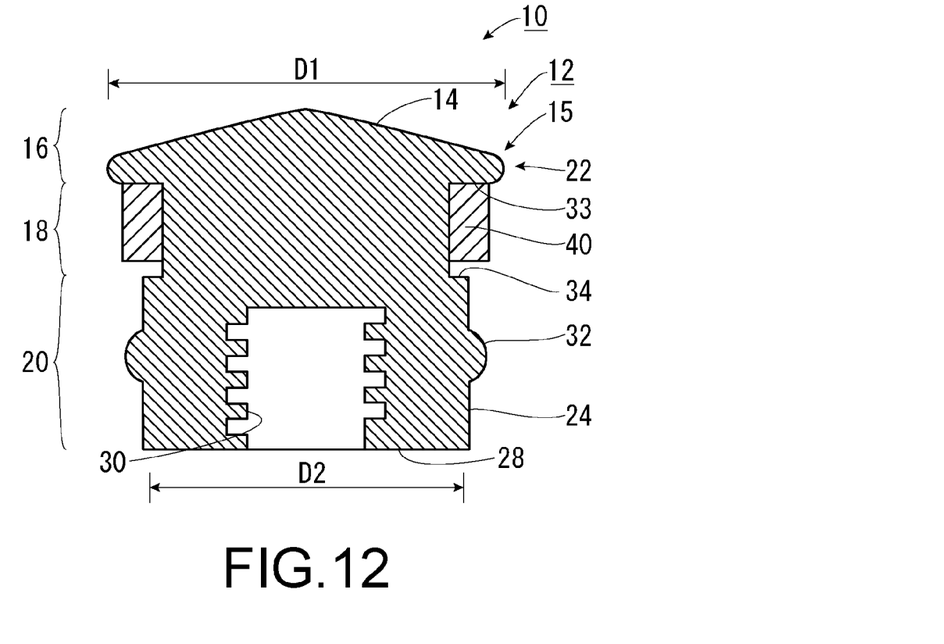
FIG. 12 is a cross-sectional view showing the gasket 10 in accordance with yet another embodiment.

Further, although the peripheral end 22 of the gasket body 12 in the above-described embodiment has a cross-sectional shape in which the tip portion 16 side is gently curved. The shape of the peripheral end 22 is not limited to this. As shown in FIG. 11, the peripheral end 22 may have a rectangular cross-sectional shape in which the tip portion 16 side is also formed in a planar shape. Further, as shown in FIG. 12, the cross-sectional shape of the peripheral end 22 may be formed in an arc shape.

Regardless of the shape, in a state in which the gasket 10 is fitted into the syringe barrel 60, it is preferable that the surface elongated by being bent the peripheral end 22 toward the rear end face 28 contacts on the inner surface 92 of the sleeve 90 and the inner peripheral surface 62 of the syringe barrel 60.

The embodiments disclosed herein are to be considered in all respects as illustrative and not restrictive. The scope of the present invention is indicated not by the above description but by the claims, and it is intended to include all modifications within the meaning and range equivalent to the claims.

10 . . . gasket, 12 . . . gasket body, 14 . . . tip surface contacting medicinal solution, 15 . . . peripheral edge portion, 16 . . . tip portion, 18 . . . small diameter portion, 20 . . . enlarged diameter portion, 22 . . . peripheral end, 24 . . . side surface, 26 . . . concave groove, 28 . . . rear end face, 30 . . . screw hole, 32 . . . ridge portion, 33 . . . leading side step, 34 . . . trailing end side step 40 . . . sliding contact ring, 50 . . . medicinal solution 60 . . . syringe barrel, 62 . . . inner peripheral surface (of the syringe barrel), 64 . . . barrel body, 66 . . . mounting portion, 68 . . . flange, 70 . . . piston rod, 72 . . . male thread portion, 74 . . . finger-pushing portion, 80 . . . top cap, 82 . . . cap body, 84 . . . cap flange, 86 . . . recess, 90 . . . sleeve, 91 . . . sleeve body, 92 . . . inner surface (of the sleeve), 94 . . . sleeve flange, 100 . . . syringe, 110 . . . conical protrusion, S . . . gap

What is claimed is:

1. A gasket, comprising:
   a gasket body made of a medicinal solution-resistant hard plastic and having a tip surface configured for contacting medicinal solution and a concave groove formed on a side surface configured for facing an inner peripheral surface of a syringe barrel and formed continuously to the tip surface configured for contacting medicinal solution; and
   a sliding contact ring made of an elastic material fitted in the concave groove,
   wherein an outer diameter of a peripheral end of a leading portion of the gasket body including the tip surface configured for contacting medicinal solution is larger than an outer diameter of the sliding contact ring,
   in a state of being fitted into the syringe barrel, a peripheral edge portion of the tip surface configured for contacting medicinal solution of the gasket body contacts against an inner peripheral surface of the syringe barrel, and
   the peripheral edge portion of the tip surface configured for contacting medicinal solution contacts the inner peripheral surface of the syringe barrel on a surface of the peripheral edge portion elongated by being bent in a state that the gasket body is fitted in the syringe barrel.

2. The gasket according to claim 1, wherein the gasket body is formed by a cold forming.

3. The gasket according to claim 1, wherein a material of the gasket body is PTFE, and the elastic material of the sliding contact ring is silicone rubber to which sliding property is added.

4. A syringe comprising:
   the gasket according to claim 1;
   medicinal solution;
   a syringe barrel; and
   a piston rod.

* * * * *